(12) United States Patent
Steffan et al.

(10) Patent No.: US 6,369,259 B1
(45) Date of Patent: Apr. 9, 2002

(54) METHOD OF PREPARING 4,5,6-TRICHLORO-AND 2,4,5,6-TETRACHLOROPYRIMIDINE

(75) Inventors: Guido Steffan, Odenthal; Georg Hardenbicker, Wipperfürth, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/668,087

(22) Filed: Sep. 22, 2000

Related U.S. Application Data

(62) Division of application No. 09/194,983, filed as application No. PCT/EP97/02933 on Jun. 6, 1997, now Pat. No. 6,162,917.

(30) Foreign Application Priority Data

Jun. 10, 1996 (DE) .......................... 196 23 064
Jun. 19, 1996 (DE) .......................... 196 24 418

(51) Int. Cl.[7] .................. C07C 255/03; C09K 19/06
(52) U.S. Cl. ..................... 558/446; 252/299.6
(58) Field of Search .................. 558/446; 252/299.6

(56) References Cited

U.S. PATENT DOCUMENTS 3,509,032 A  4/1970  Beck et al. ............... 204/158

5,051,507 A  * 9/1991  Schundehutte et al. ..... 544/334

OTHER PUBLICATIONS

Chemical Abstracts, vol. 106, No. 28, Abstract No. 176415K.
Angewandte Chemie International Edition vol. No. 3, (month unavailable) 1974, G. Beck, Highly Chlorinated Systems by Ring Closure Reactions, p. 210.

* cited by examiner

*Primary Examiner*—Floyd D. Higel
*Assistant Examiner*—Ebenezer Sackey
(74) *Attorney, Agent, or Firm*—Joseph C. Gil; Diderico van Eyl

(57) ABSTRACT

Crystals with an average crystal size of $\leq 10\,\mu$m comprising compounds of the formula Ia and/or IIa

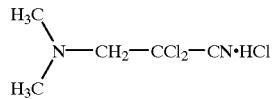

(Ia)

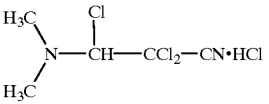

(IIa)

A process for making said crystals.

2 Claims, No Drawings

METHOD OF PREPARING 4,5,6-TRICHLORO-AND 2,4,5,6-TETRACHLOROPYRIMIDINE

This application a divisional of U.S. Ser. No. 09/194,983 filed on Dec. 7 1998 now U.S. Pat. No. 6,162,917 which is a 371 of PCT/EP97/02933 filed Jun. 6, 1999.

FIELD OF THE INVENTION

The invention relates to a process for the preparation of 4,5,6-trichloro- and 2,4,5,6-tetrachloropyrimidine starting from 3-dimethylaminopropionitrile, to its use and also to a crystalline intermediate product form.

BACKGROUND OF THE INVENTION

According to US-A 3 509 032, 4,5,6-trichloro- and 2,4,5,6-tetrachloropyrimidine are obtained by chlorination of 3-dimethylaminopropionitrile with $Cl_2$ with irradiation by UV light, it being necessary for the temperature of the chlorination to sometimes be above 150° C., in particular from 180 to 220° C., in order to permit the desired products to form (see column 2, line 51 to 53 and Example 2 and 3). Such high chlorination temperatures are, however, disadvantageous when carrying out the procedure industrially.

According to DE-A 3 900 917, 4,5,6-trichloropyrimidine is prepared from the hydrochloride of 3-dimethylaminopropionitrile in a single-step chlorination at a temperature of from 120 to 130° C. However, some aspects of this procedure can still be improved upon, in particular as regards its suitability for large-scale batches.

Furthermore, most of the processes described in the prior art have the disadvantage that during subsequent distillation insoluble distillation residues are formed, which can only be removed from the distillation vessels at considerable expense. In addition, the resulting products gas very severely during distillation.

The object of the present invention was therefore to provide a process for the preparation of 4,5,6-trichloro- and 2,4,5,6-tetrachloropyrimidines starting from 3-dimethethylaminopropionitrile which does not have the above disadvantages.

DETAILED DESCRIPTION OF THE INVENTION

We have found a process for the preparation of 4,5,6-trichloro- and 2,4,5,6-tetrachloropyrimidine by reacting 3-dimethylaminopropionitrile with HCl and $Cl_2$, which comprises
  a) in a first reaction step reacting 3-dimethylaminopropionitrile in a solvent, preferably one inert towards HCl and $Cl_2$, with HCl, preferably from 1 to 6 mol, and $Cl_2$, preferably from 2 to 4 mol, in each case based on 1 mol of 3-dimethylaminopropionitrile, at a temperature of from −10 to 55° C., and
  b) in a second reaction step reacting the reaction mixture from the first reaction step with $Cl_2$, preferably from 3 to 5 mol, based on 1 mol of 3-dimethylaminopropionitrile used, at a temperature above 55° C., preferably from 65 to 120° C., optionally in the presence of a catalyst,
characterized in that the second reaction step is carried out in the presence of the reaction product from the first reaction step, which is in microcrystalline form with an average crystal size of ≦10 μm.

DETAILED DESCRIPTION OF THE INVENTION

The solvents which are inert towards HCl and $Cl_2$ under reaction conditions are preferably taken to mean those which are inert under the specified reaction conditions of the process according to the invention. Examples of suitable solvents are chlorinated, aliphatic and aromatic hydrocarbons, such as chloroform, tetrachloromethane, chlorobenzene, dichlorobenzene, isododecane, phosphorus oxychloride or mixtures thereof. Particular preference is given to phosphorus oxychloride ($POCl_3$).

The first reaction step of the process according to the invention is preferably carried out at a temperature of from 15 to 25° C. It can, for example, be carried out batchwise or continuously.

The batchwise process variant involves, for example, initially introducing the 3-dimethylaminopropionitrile, preferably in the solvent inert towards $Cl_2$ and HCl, and passing HCl into it. The amount of HCl to be introduced is generally from 1 to 6 mol, preferably from 3 to 4 mol, based on 1 mol of the 3-dimethylaminopropionitrile used. The resulting HCl adduct of the nitrile is particularly readily soluble in the temperature range according to the invention when the solvent used is phosphorus oxychloride. The heat produced during HCl introduction with HCl adduct formation is preferably dissipated by cooling. This is then followed by the reaction with preferably from 2 to 4 mol of $Cl_2$ per mole of 3-dimethylaminopropionitrile. To this end, $Cl_2$ is passed into the reaction mixture for the HCl reaction with evolution of HCl. The introduction is preferably carried out at from 15 to 20° C.

The above-described batchwise variant preferably involves introducing from 1 to 2 mol of HCl before starting to introduce $Cl_2$. The HCl adduct formation of the nitrile is then completed by the HCl formed during the chlorination.

The batchwise process variant is preferably chosen for small batches, in particular for batches smaller than 10 mol, based on 3-dimethylaminopropionitrile.

Particular preference is given to carrying out the reaction of the first reaction step of the process according to the invention continuously. In the continuous method, the solvent inert towards $Cl_2$ and HCl, in particular phosphorus oxychloride, 3-dimethylaminopropionitrile, HCl and $Cl_2$ are preferably brought together continuously in a reactor. The amount of HCl is preferably from 1 to 2 mol per mole of 3-dimethylaminopropionitrile.

The amount of $Cl_2$ corresponds to that mentioned at the outset. The HCl formed during the chlorination preferably remains in the reaction mixture and thus does not need to be fed in from outside. The heat which is liberated during the reaction is preferably dissipated by cooling. The temperature for the continuous method is particularly preferably maintained at from 15 to 25° C.

The reaction in the 1st reaction step is particularly preferably carried out completely continuously, this being taken to mean the continuous introduction of reactants and the continuous removal of reaction product.

If phosphorus oxychloride is used as preferred solvent, the reaction mixture in the first reaction step which is formed continuously is in the form of a solution at a temperature of from −10 to +55° C.

The reaction products formed in the first reaction step of the process according to the invention are preferably the hydrochlorides of the chlorinated 3-dimethylaminopropionitrile, which preferably conform to the formulae (I) and (II)

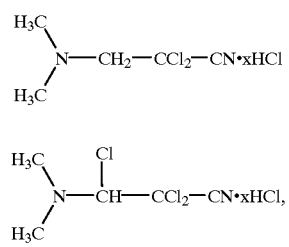

(I)

(II)

in which x is a number from 1 to 3, preferably 3.

With particular preference, a product mixture is formed in which the compounds of the formulae (I) and (II) are present in a ratio of from 10:1 to 2:1.

The amount of solvent used can be varied over wide ranges. It is preferable to use from 4 to 10 parts of solvent per part of 3-dimethylaminopropionitrile used.

In a particularly preferred embodiment of the process according to the invention, the reaction mixture from the first reaction step and further $Cl_2$ are brought together semi-continuously at the temperature of the second reaction step, i.e. such that the bringing together, preferably in a second reactor, takes place for as long as the size of this reactor permits filling. In this connection, any catalyst which is used can, for example, be introduced with the introduced reaction mixture of the first reaction step or, for example, already be present in the reactor.

In the second reaction step HCl is formed. It is formed on the one hand during the chlorination and is, on the other hand, liberated from the HCl adduct of the first reaction step to form a monohydrochloride.

Transferring the reaction mixture of the first reaction step to the second step, preferably to the second reactor, results in crystalline precipitation. Furthermore, transfer to the second reaction step, which proceeds at a higher temperature (compared with the first reaction step) leads to the evolution of HCl. When the reaction mixture is transferred to the 2nd reaction step, coarse crystalline precipitations initially form. After a short time, finer crystals (microcrystals) can then be observed.

Both the coarse and also the fine crystals are crystals or mixed crystals of monohydrochlorides of the formulae (Ia) and/or (IIa).

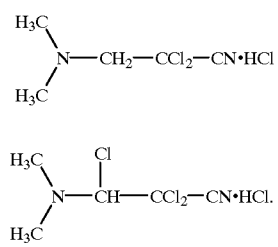

(Ia)

(IIa)

These initially precipitate as relatively coarse crystals which have an average crystal size of >10 μm. These coarse crystals preferably precipitate in the form of colourless platelets which are cuboid and have an edge length of from 0.05 to 0.2 mm and a thickness of about 0.01 mm. These crystals preferably comprise the compounds Ia and IIa in a weight ratio of from 10:1 to 2:1.

The invention also relates to crystals with an average crystal size of ≦10 μm comprising the compounds of the formula Ia and/or IIa.

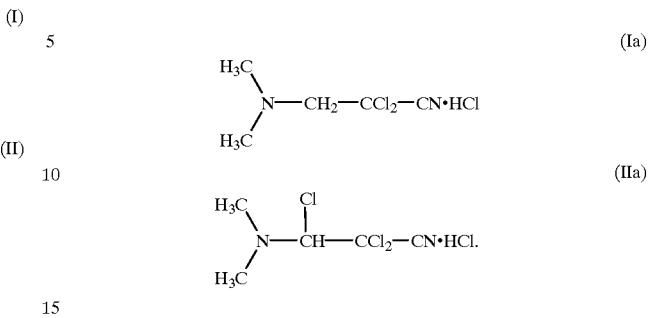

(Ia)

(IIa)

These preferably comprise the compounds of the formulae Ia and IIa in a weight ratio of from 10:1 to 2:1.

The microcrystals are preferably in the form of needles or rods which have a length of from 2 to 6 μm and a thickness of from 0.5 to 1 μm.

The invention further relates to a process for the preparation of these microcrystals, which is characterized in that 3-dimethylaminopropionitrile in a solvent which is inert towards HCl and $Cl_2$ is reacted with from 1 to 6 mol of HCl and from 2 to 4 mol of $Cl_2$, in each case based on 1 mol of 3-dimethylaminopropionitrile, at a temperature of from −10 to 55° C., and then the resulting reaction mixture is heat-treated at a temperature of from 65 to 85° C.

In a particularly preferred embodiment of the process according to the invention for the preparation of the chloropyrimidines, the ratio of microcrystals to a coarse crystalline form is from 95:5 to 50:50.

The process according to the invention is particularly suitable for batches >1 kmol, based on 3-dimethylaminopropionitrile.

The second reaction step preferably follows the 1st reaction step immediately, so that the residence time between the two steps is kept as short as possible.

If the finely crystalline monohydrochloride is isolated, it can be used as seed crystals for the second reaction step. In this case, the same advantageous effect is achieved, even without awaiting the formation of fine crystalline precipitation.

The reaction product of the 1st reaction step is preferably transferred to the second reactor such that the fraction of the microcrystals, which only form slowly, relative to the coarse crystalline form does not become too small since it has been found that the coarse crystalline form is unstable under the reaction conditions. The ratio of microcrystals to the coarse crystalline form is preferably from 95:5 to 50:50.

In a very particularly preferred embodiment of the second reaction step, the reaction is carried out in the presence of a catalyst. Possible catalysts which may be mentioned are, for example, organic catalysts. Suitable organic catalysts are, for example, open-chain or cyclic carboxamides, such as $C_1$-$C_{12}$-dialkylformamides, in particular dimethylformamide, dibutylformamide, methyldodecylformamide, N—$C_1$-$C_{12}$-alkylpyrrolidones, such as N-methyl-2-pyrrolidone, N—$C_1$-$C_{12}$-alkylcaprolactams, such as N-methylcaprolactam, and also trialkyl phosphites, triaryl phosphites, triarylphosphine oxides, where aryl is preferably optionally substituted phenyl. Particular preference is given to triphenylphosphine oxide.

The catalysts can also be used in a mixture with one another, preferably in amounts of from 1 to 10% by weight, preferably from 2 to 5% by weight, based on 3-dimethylaminoproplonitrile used.

The second reaction step of the process according to the invention is very particularly preferably carried out in the presence of free-radical scavengers. Preference is given to oxygen, in particular in the form of air. Air is, for example, preferably introduced into the reaction mixture in an amount of from 10 to 100 l per 1 kg of 3-dimethylaminopropionitrile used, in particular continuously throughout the reaction period.

Very particular preference is given to the process according to the invention in which the HCl formed in the second reaction step, optionally together with excess $Cl_2$ from the second reaction step, is returned to the first reaction step, as a result of which it is not necessary to introduce more HCl from outside. The process according to the invention in a particularly preferred embodiment is thus autarkic with respect to HCl.

The process according to the invention preferably produces 4,5,6-trichloro- and 2,4,5,6-tetrachloropyrimidine as a mixture. The composition in favour of one of the two pyrimidines can preferably be controlled via the temperature. In this connection, the trichloropyrimidine, for example, for the same reaction time, is preferably formed at a reaction temperature of from 85 to 105° C., whilst the 2,4,5,6-tetrachloropyrimidine is preferably formed at a temperature of from 65 to 75° C. Chloropyrimidine mixtures obtained in this way preferably have a ratio of trichloro- to tetrachloropyrimidine of from 4:1 to 1:30.

The resulting 4,5,6-trichloro- and 2,4,5,6-tetrachloropyrimidine and the solvent used are preferably fractionally distilled for the purposes of isolation and recovery. After the respective product has been distilled off, it is possible to obtain in each case a second fraction of the product from the distillation residue in the presence of a little activated carbon. The relatively small amount of distillation residues which remain are readily soluble in, for example, o-dichlorobenzene, and can in this form, for example, be incinerated.

4,5,6-Trichloro- and 2,4,5,6-tetrachloropyrimidine are, for example, important intermediates for the preparation of fluorine-containing reactive components, such as those incorporated into reactive dyes (see DE-A 1 644 203), and are also suitable as intermediates for crop-protection compositions and pharmaceuticals.

The invention is further described in the following illustrative examples. All parts are by weight, unless otherwise noted.

EXAMPLES

Example 1

Preparation of 4,5,6-trichloropyrimidine

Two reactors 1 and 2 connected one behind the other were each initially charged with 85 g (50 ml) of phosphorus oxychloride. 5 g of triphenylphosphine oxide were also added to the further of the two reactors (reactor 2). The reaction is carried out in the absence of water.

At a temperature maintained at from 15 to 20° C. by cooling the following were uniformly metered into reactor 1 over the course of 13 hours:

1. a solution of 600 g (6.12 mol) of 3-dimethylaminopropionitrile in 3340 g of phosphorus oxychloride,
2. about 500 g (17.7 mol) of hydrogen chloride and
3. about 850 g (12 mol) of chlorine, The hydrogen chloride and chlorine metering rates chosen being initially slightly higher and, after the 2nd reactor has been started up, being slightly reduced since the offgas from reactor 2 was co-used in reactor 1.

The amount of reaction mixture in reactor 1 was maintained at from 50 to a maximum of 100 ml by pumping off or overflow into reactor 2.

As soon as the reaction mixture overflowed as a clear solution from reactor 1 into reactor 2, it was seeded with from 200 to 300 mg of the microcrystals obtained according to Example 4, and then the metering in of 2300 g (32.4 mol) of chlorine over the course of 13 hours and of dry air (about 0.5 ml per second) into reactor 2 was started, the metering in into reactor 2 initially being carried out at a temperature of about 85° C. After offgas began to escape from reactor 2, a jet washer over reactor 1 was put into operation in order to utilize there the offgas from reactor 2.

The temperature in reactor 2 was then increased firstly to from 95 to 97° C. and after a further hour to from 102 to 104° C. and maintained at that for 13 hours. After 5 and 13 hours, a further 5 g of triphenylphosphine oxide were each time metered into reactor 2.

After reactor 2 (capacity=4 l) was virtually full, and all of the product feeds into reactor 1 had been stopped, the latter was completely emptied into reactor 2.

Over the course of a further 12 hours, about 1100 g (15.5 mol) of chlorine (and also the aforementioned amount of air) were then introduced into reactor 2 at a gradually decreasing metering rate such that initially the offgas was virtually colourless and later only slightly green.

The end of the reaction is reached as soon as the reaction mixture in reactor 2, which turns milky, gradually changes into a clear bright solution. This was then followed by work-up.

Work-up

Phosphorus oxychloride, which was reused, was firstly completely distilled off from the resulting solution over a column. About 3350 g of phosphorus oxychloride were obtained. 1048 g of a mixture of tri- and tetrachloropyrimidine were then distilled off under reduced pressure, heating being carried out up to a maximum still temperature of 180° C. at 12 mbar.

After 5 g of dry activated carbon had been added to the distillation residue, the latter was heat-treated at 195° C. for 1 hour with the release of small amounts of chlorine. Then, at from 10 to 12 mbar and up to a maximum still temperature of 200° C., a further 54 g of product mixture were obtained. The residue (81 g, including 15 g of triphenylphosphine oxide derivative and 5 g of activated carbon) was stirred with 50 g of 1,2-dichlorobenzene to give a low-viscosity suspension.

Together with about 1% of product mixture in the phosphorus oxychloride distillate, a total (according to GC analysis) of 756 g of 4,5,6-trichloropyrimidine (=68% of theory, based on 3-dimethylaminopropionitrile used) and 348 g of tetrachloropyrimidine (=26.5% of theory, based on 3-dimethylaminopropionitrile used) were obtained, which were separated by rectification. This corresponds to an overall yield of 94.5% of theory, when using 99% strength 3-dimethylaminopropionitrile.

The same results were also obtained for 10 to 12 mol and also for 1 to 2 kmol batches, whilst when the process was carried out as is known from DE-A 3 900 917, the yield dropped from between 95 and 90% for 0.5 to 2 mol batches, to between 75 and 70% for 10 to 12 mol batches and to between 65 and 60% for 1–2 kmol batches, in each case based on 3-dimethylaminopropionitrile used.

Example 2

Preparation of 2,4,5,6-tetrachloroprymidine

Two reactors 1 and 2 connected one behind the other (as in Example 1) were initially charged with 85 g (50 ml) of phosphorus oxychloride in reactor 1 and 125 g (75 ml) of phosphorus oxychloride and 5 g of triphenylphosphine oxide in the rear reactor (reactor 2).

At a temperature maintained at from 15 to 20° C. by cooling, the following were uniformly metered into reactor 1 over the course of 16 ¾ hours:

1. a solution of 600 g (6.12 mol) of 3-dimethylaminopropionitrile in 3300 g of phosphorus oxychloride,
2. about 600 g (19.5 mol) of hydrogen chloride and
3. about 890 g (12.53 mol) of chlorine, the hydrogen chloride and chlorine metering rates initially being set slightly higher (about 40 g of HCl/h and about 55 to 60 g of chlorine/h), and after the 2nd reactor has been started being slightly reduced as the offgas from reactor 2 was co-used in reactor 1.

The amount of reaction mixture in reactor 1 was kept at from 50 to a maximum of 100 ml by allowing it to continuously flow over into reactor 2.

As soon as the reaction mixture transferred from reactor 1 to reactor 2 as a solution, at a temperature of about 75° C. the introduction of 3600 g (50.7 mol) of chlorine over the course of 16¾ hours and of dry air (about 0.5 ml per second) was started.

Shortly thereafter, from 200 to 300 mg of seed crystals of the finely crystalline monohydrochloride mixture of 2,2-dichloro- and 2,2,3-trichloro-3-dimethylaminopropionitrile were added to reactor 2.

As soon as the offgas from reactor 2 began to escape, a jet washer over reactor 1 was put into operation in order to utilize there the offgas from reactor 2. The temperature in reactor 2 was maintained at from 74 to 76° C. throughout the entire 16¾ hours. After 7 and 14 hours of the 16¾ hours, a further 5 g of triphenylphosphine oxide were each time metered into reactor 2.

As soon as reactor 2 (capacity=4 l) was virtually full at the end of 16¾ hours, all metered additions into reactor 1 were stopped and the contents of the latter were transferred to reactor 2.

Over the course of a further 22.5 hours, 820 g (11.55 mol) of chlorine and also the abovementioned amount of air were introduced into reactor 2 with a gradually decreasing metering rate so that the offgas was always only slightly green in colour. After 8 hours of the 22.5 hours, 5 g of triphenylphosphine oxide were also added. The temperature was maintained throughout the first 14 hours at from 74 to 76° C., and then in a further 8 hours, gradually increased from 80 to 90° C. and in the last half an hour, after the reaction mixture in reactor 2, which appears milky, had gradually changed into a clear bright solution, maintained at 95° C.

The phosphorus oxychloride was initially completely distilled off from the resulting solution over a column. About 3410 g of phosphorus oxychloride were obtained. 1105 g of a mixture of tri- and tetrachloropyrimidine were then distilled off under reduced pressure, heating being carried out up to a maximum still temperature of 180° C. at 12 mbar.

After 5 g of dry activated carbon had been added, the distillation residue was heat-treated at 195° C. for one hour with the release of small amounts of chlorine. A further 122 g of product mixture were then obtained at from 10 to 12 mbar and up to a maximum still temperature of 205° C.

The residue (105 g, including about 20 g of triphenylphosphine oxide derivatives and 5 g of activated carbon) were still liquid at 130° C. and were stirred with 100 g of 1,2-dichlorobenzene to give a suspension which was also still low-viscosity at room temperature.

Together with about 0.5% of the product of the product mixture in the phosphorus oxychloride distillate, a total (according to GC analysis) of 102 g of 4,5,6-trichloropyrimidine (=9.2% of theory, based on 3-dimethylaminopropionitrile) and 1139 g of tetrachloropyrimidine (=86.2% of theory, based on 3-dimethylaminopropionitrile) were thus obtained, which were separated by rectification. This corresponds to an overall yield of 95.4% of theory using 99% strength dimethylaminopropionitrile. The same yields were also obtained in 10 and 12 mol batches.

Example 3

The procedure was the same as in Example 2, although the period of continuous chlorination was extended from 16¾ hours to 19 hours, the temperature in reactor 2 being maintained at 70° C., and subsequently chlorination being carried out for 19 hours at 70° C., for 6 hours at from 75 to 80° C., for 4 hours at from 80 to 85° C. and for 90° C. A yield of 93% of theory, based on 3-dimethylaminopropionitrile used, of tetrachloropyrimidine and 3% of theory of 4,5,6-trichloropyrimidine was obtained.

Example 4

Preparation and characterization of the coarse and microcrystalline forms of 2,2-dichloro-3-dimethylaminopropionitrile monohydrochloride and the microcrystalline form of 2,2,3-trichloro-3-dimethylaminopropionitrile monohydrochloride a) 100 g of a HCl gas were initially introduced into a mixture of 580 g of phosphorus oxychloride and 100 g of 3-dimethylamino-propionitrile (about 98% strength) at from 15 to 25° C. in about 45 minutes with cooling, and then 142 g of chlorine were introduced into the resulting clear solution with powerful cooling at from 10 to 15° C. in about 30 minutes. The resulting clear solution was heated rapidly (in about 10 minutes) to 50° C., still very little chlorine (about 5 g) being introduced and a large amount of HCl being outgassed. Very soon coarse clear crystals separated out.

b) Half of the reaction mixture obtained in a) was filtered through a glass sinter suction filter, and the resulting crystals were washed with toluene and petroleum ether in order to free them from phosphorus oxychloride, and dried under reduced pressure at 50° C. for 2 hours. 76 g of colourless platelets were obtained, which were identified by elemental analysis, mass and NMR spectrum as monohydrochloride of 2,2-dichloro-3-dimethylamine-propionitrile. These were cuboid platelets with an edge length of from 0.05 to 2 mm and a thickness of 0.01 mm.

c) The second half of the abovementioned reaction mixture was heated to 75° C. After about 10 minutes, the abovementioned coarse platelets converted to a very fine crystalline mass, as a result of which the reaction mixture became very viscous. After 10 to 15 minutes of further heat-treatment to complete conversion, the crystals were filtered as above, and washed and dried. 74 g of colourless microcrystals were obtained, which are identified by elemental analysis, gas chromatography, mass and NMR spectrum as a mixture of about 90 mol per cent of the abovementioned monohydrochloride of 2,2-dichloro-3-dimethylaminopropionitrile and about 10 mol per cent of the monohydrochloride of 2,2,3-trichloro-3-dimethylaminopropionitrile.

The microscopic investigation showed that the microcrystals are produced in the form of needles or rods having a length of from 2 to 6 micrometers and from about 0.5 to 1 micrometer in thickness, which were largely agglomerated.

d) A further batch was likewise carried out, as described under a) but introducing a further 35 g of chlorine instead of 5 g upon heating to 50° C.

The mixture was then—as described under c)—heated to 75° C., and chlorine was further introduced (a total of about another 40 g).

After about 15 minutes, the coarse platelets, which crystallized out upon warming to 50° C., converted to fine crystals, which were isolated after heat treatment for a further 15 minutes as described.

The investigations carried out above showed that the product is virtually pure monohydrochloride of 2,2,3-trichloro-3-dimethylaminopropionitrile. The microscopic investigation showed the same crystal habit as the aforementioned corresponding mixture of dichloro and trichloro derivative.

Example 5
(Tetrachloropyrimidine in 1000 l Reactor)

165 kg of phosphorus oxychloride (100 l) and 1.5 kg of triphenylphosphine oxide were heated to 75° C. in a 1000 l steel enamel reactor (with gas inlet through the bottom valve. A 25 l glass reactor (with intensive salt water cooling) which was positioned above was charged with 16 kg of phosphorus oxychloride (about 10 l).

The following were then metered into the 25 l glass reactor uniformly and simultaneously over the course of 17 hours:

980 kg of phosphorus oxychloride
180 kg of 3-dimethylaminopropionitrile
120 kg of hydrogen chloride and
274 kg of chlorine the temperature being maintained at from 10 to 15° C. with intensive thorough mixing and cooling.

The reaction volume in the 25 l glass reactor was maintained at 20 l by overflow into the 1000 l steel enamel reactor. As soon as product overflowed from the 25 l reactor into the 1000 l reactor, 50 g of seed crystals (microcrystals of 2,2-dichloro- and 2,2,3-trichloro-3-dimethylaminopropionitrile monohydrochloride/preparation see Example 4) were added thereto.

A total of 762 kg of chlorine (and per hour about 100 l of dry air) were uniformly metered into the 1000 l reactor through the bottom valve at 75° C. over the course of a total of 17 hours. During these 17 hours, 1.5 kg of triphenylphosphine oxide were added to the 1000 l reactor each time after 7 and 13 hours.

At the end of these 17 hours, the contents of the glass reactor were discharged into the 1000 l reactor.

Over the course of a further 21 hours, a total of 166 kg of chlorine (and also the abovementioned amount of air) were then metered into the 1000 l reactor in such a way that the offgas was always slightly green in colour. After 9 of these 21 hours, a further 1.5 kg of triphenylphosphine oxide were added.

The temperature in the 1000 l reactor was maintained at from 74 to 76° C. during the first 14 hours of these 21 hours, then increased slowly to 88° C. in 6 hours. Following complete dissolution of the crystals, the temperature was increased to 95° C. and maintained at that for a further ½ hour.

The phosphorus oxychloride was first virtually completely distilled off from the resulting solution via a 5-plate column at a reflux ratio of 1:1 (at a pressure gradually reduced to 60 mbar). The mixture of tri- and tetrachloropyrimidine (326 kg) were then distilled off at from 10 to 12 mbar up to a still temperature of 183° C.

After 2 kg of dry activated carbon had been added, the distillation residue was heat treated at 195 to 200° C. for 2 hours (moderate chlorine release). Then, at from 9 to 12 mbar and up to a maximum still temperature of 212° C., a further 44.5 kg of product mixture are obtained by distillation.

According to the gas chromatogram, the 370.5 kg of product mixture comprised 5.6% by weight of 4,5,6-trichloropyrimidine and 94.3% by weight of tetrachloropyrimidine, which corresponds to an overall yield of 94.3% of theory.

After 40 kg of 1,2-dichlorobenzene had been added, the distillation residue could be removed completely from the distillation vessel (a total of 73 kg, including 40 kg of 1,2-dichlorobenzene).

Example 6
(4,5,6-Trichloropyrimidine in 1000 l Reactor)

In the same apparatus as described in Example 5, the 1000 l reactor was charged with 165 kg of phosphorus oxychloride (100 l) and 1.5 kg of triphenylphosphine oxide (mixture heated to 85° C.), and the 25 l reactor was charged with 16 kg of phosphorus oxychloride (10 l).

The following were then added uniformly and simultaneously to the 25 l reactor at from 10 to 15° C. over the course of 14 hours:

995 kg of phosphorus oxychloride
180 kg of 3-dimethylaminopropionitrile
115 kg of hydrogen chloride and
266 kg of chlorine.

The reaction volume in the 25 l reactor was maintained at 20 l by overflow into the 1000 l reactor.

As soon as product overflowed from the 25 l reactor into the 1000 l reactor about 100 g of seed crystals (microcrystal mixture of 2,2-dichloro- and 2,2,3-trichloro-3-dimethylaminopropionitrile monohydrochloride/preparation see Example 4) were added thereto.

A total of 675 kg of chlorine (and per hour about 100 l of dry air) were then uniformly metered into the 1000 l reactor through the bottom valve over the course of a total of 14 hours, the initial temperature increasing rapidly from 85° C. to 95 to 97° C., and after a further hour to 103 to 105° C. and being maintained at that until the end of the 14 hours. During these 14 hours 1.5 kg of triphenylphosphine oxide were additionally added to the reactor each time after 6 and 13 hours). At the end of these 14 hours, the contents of the 25 l reactor were discharged into the 1000 l reactor.

Over the course of this time, a clear bright solution gradually formed from the suspension of microcrystals.

This solution was then worked up as described in Example 5.

Altogether the following amounts were obtained:
328 kg of product distillate which, according to the gas chromatogram, comprises
72.2% by weight of 4,5,6-trichloropyrimidine and
27.6% by weight of tetrachloropyrimidine
which corresponds to an overall yield of 93.8% of theory.

Following the addition of 40 kg of 1,2-dichlorobenzene, the distillation residue was able to be removed from the distillation vessel completely (total 67 kg, including 40 kg of 1,2-dichlorobenzene).

Although the invention has been described in detail in the foregoing for the purpose of illustration, it is to be under-

What is claimed is:

1. Crystals with an average crystal size of ≦10 μm, wherein the crystals are compounds having the formula Ia, or IIa:

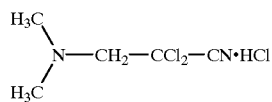
(Ia)

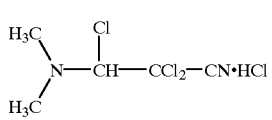
(IIa)

2. A process for preparing the crystals with an average crystal size of ≦10 μm, wherein the crystals are compounds having the formula Ia, or IIa:

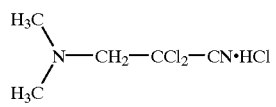
(Ia)

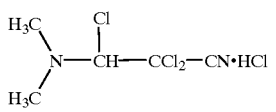
(IIa)

the process comprising reacting:

1) 3-dimethylaminopropionitrile in a solvent which is inert towards HCl and $Cl_2$ with
2) from 1 to 6 mol of HCl and from 2 to 4 mol of $Cl_2$, in each case based on 1 mol of 3-dimentylaminopropionitrile, at a temperature of from 10 to 55° C., and then
3) heat-treating the resulting reaction mixture at a temperature of from 65 to 85° C.

* * * * *